United States Patent
Winchell et al.

(10) Patent No.: US 6,576,760 B2
(45) Date of Patent: Jun. 10, 2003

(54) PROCESSES FOR SYNTHESIS OF CYCLIC AND LINEAR POLYAMINE CHELATORS CONTAINING N-MONOSUBSTITUTED COORDINATING ARMS

(75) Inventors: Harry S. Winchell, Lafayette, CA (US); Rosa L. Cyjon, Haifa (IL); Joseph Y. Klein, Haifa (IL); Elliot D. Simhon, Haifa (IL); Ofer Klein, Haifa (IL); Haim Zaklad, Haifa (IL)

(73) Assignee: Chelator LLC, Concord, CA (US)

( * ) Notice: Subject to any disclaimer, the term of this patent is extended or adjusted under 35 U.S.C. 154(b) by 0 days.

(21) Appl. No.: 09/759,092

(22) Filed: Jan. 11, 2001

(65) Prior Publication Data

US 2002/0091253 A1 Jul. 11, 2002

(51) Int. Cl.$^7$ ............ C07D 245/00; C07D 223/00; C07D 221/02; C07F 9/06; C07F 9/02
(52) U.S. Cl. .......... 540/202; 540/460; 540/471; 540/472; 540/473; 540/474; 540/487; 544/214; 544/243; 544/244; 544/337; 546/22; 546/23; 546/24; 548/112; 548/113
(58) Field of Search ............... 540/202, 460, 540/471, 472, 473, 474, 487, 542; 544/214, 243, 244, 337; 546/22, 23, 24; 548/112, 113

(56) References Cited

U.S. PATENT DOCUMENTS

| | | | |
|---|---|---|---|
| 5,236,695 A | 8/1993 | Winchell et al. | 424/9 |
| 5,380,515 A | 1/1995 | Winchell et al. | 424/9 |
| 5,409,689 A | 4/1995 | Winchell et al. | 424/9 |
| 5,593,659 A | 1/1997 | Winchell et al. | 424/9 |
| 5,874,573 A | 2/1999 | Winchell et al. | 540/465 |

OTHER PUBLICATIONS

Helps et al.: "Syntheses of C– and N–Functionalised Derivtives of 1,5,9–Triazacyclododecane" *J. Chem. Soc. Perkin Trans. I* (1989), (11) 2079–2082.

Krakowiak et al.: "Improved Methods for the Synthesis of Aza–Crown Macrocycles and Cryptands" *Dept. of Chem.*, Brigham Young Univ., Provo, Utah 611–620 Synlett, Sep. 1993 (9).

Parker: "Aza Crowns" in Macrocycle Synthesis, A Practical Approach, 1–23, *Oxford Univ. Press* (1996).

Wainwright: "Synthetic and structural aspects of the chemistry of saturated polyaza macrocyclic ligands bearing pendant coordinating groups attached to nitrogen" in Coordination Chemistry Reviews 166: 35–90 *Elsevier Science S.A.* (1997).

Rivkin et al.: "IRC011, a New Synthetic Chelator With Selective Interaction With Catabolic Red Blood Cell Iron: Evaluation in Hypertransfused Rates With Hepatocellular and Reticuloendothelial Radioiron Probes and in Iron-Loaded Rat Heart Cells in Culture", 90:4180–4187 *Blood* (1997).

Bradshaw et al.: "Common Methods for the Formation of Polyaza Macrocyclic Rings", in Aza–Crown Macrocycles, 123–171 *John Willey & Sons, Inc.*, 1993.

Harefield et al.: "(1,48,11–Tetraazacyclotetradecancane) Nickel(II) Perchlorate and 1,4,8,11–Tetraazacyclothetradecane", 220–225, Inorganic Syntheses, 16, (1976).

*Primary Examiner*—Brenda Coleman
(74) *Attorney, Agent, or Firm*—Townsend and Townsend and Crew LLP

(57) ABSTRACT

Polyamines containing at least two nitrogen atoms monosubstituted with pendant arms capable of coordinating metal cations, or with precursors of such pendant arms, all nitrogen atoms of the polyamines except two being fully substituted and the remaining two bearing one H atom each, are cyclized by reaction with a bridging agent that contains two sites that each bear a reactive group capable of undergoing a nucleophilic attack by one of the two N-H groups on the polyamine. Unlike the prior art, cyclization occurs in preference over polymerization of the polyamine, even in reaction mixtures in which the polyamine is at high concentration. A process is also disclosed whereby linear polyamines in which the terminal amine groups are primary amines are substituted with methylenephosphonate ester groups, with one such substituent on each nitrogen atom of the polyamine. The process involves the use of a trialkyl or triaryl phosphite, and unlike the prior art, monosubstitutions at all nitrogen atoms are achieved in preference over disubstitutions at the terminal primary amines. Finally, a novel class of N,N',N"-tris(methylenephosphonate or methylephosphonic acid-substituted)-1,4,7-triazaheptanes are disclosed as new compositions of matter.

1 Claim, No Drawings

PROCESSES FOR SYNTHESIS OF CYCLIC AND LINEAR POLYAMINE CHELATORS CONTAINING N-MONOSUBSTITUTED COORDINATING ARMS

BACKGROUND OF THE INVENTION

1. Field of the Invention

This invention resides in the field of alkylation reactions, cyclization reactions, and reactions involving substitutions at a nitrogen atom.

2. Description of the Prior Art

Cyclic polyamine chelators, which are cyclic amines whose nitrogen atoms have pendant arms attached thereto that are capable of coordinating metal cations, have a wide range of utility. Chelators of this type are disclosed by Lindoy, L. F., *The Chemistry of Macrocyclic Ligand Complexes,* University Press, Cambridge, 1989; and Bradshaw, J. S., et al., *The Chemistry of Heterocyclic Compounds,* John Wiley & Sons, New York, 1993, vol. 51. One use of these chelators is in the treatment of conditions caused by an excess of first transition series elements in the body. Iron overload anemias are examples of such conditions. See Rivkin, G., et al., *Blood,* vol. 90, no. 10, pp. 4180–4187 (Nov. 15, 1997). Another use is in altering the expression of enzymes containing first transition series metal cations as co-enzymes and by inhibiting replication of mammalian, parasitic, fungal, and bacterial cells and viruses. A disclosure of this use appears in Winchell, H. S., et al., U.S. Pat. No. 5,874,573, issued Feb. 23, 1999. A further use is in the formation of complexes with radioisotopic or paramagnetic metal cations. These complexes are useful in diagnostic radioisotopic and magnetic resonance imaging, and disclosures of how these complexes are used in this manner uses are found in Winchell, H. S., et al., U.S. Pat. Nos. 5,236,695, issued Aug. 17, 1993, 5,380,515, issued Jan. 10, 1995, 5,593,659, issued Jan. 14, 1997, and 5,409,689, issued Apr. 25, 1995.

Known methods for the synthesis of N-substituted cyclic polyamine begin with a laborious and costly multi-step synthesis of the unsubstituted cyclic polyamine. Additional steps are then performed to attach the chelating pendant arms to nitrogen atoms. These methods are disclosed by Parker, D., *Aza Crowns in Macrocyclic Synthesis,* Oxford Universtiy Press, Oxford, U. K., 1996, and by Wainwright, K. P., "Synthetic and Structural Aspects of the Chemistry of Saturated Polyaza Macrocyclic Ligands Bearing Pendant Coordinating Groups Attached to Nitrogen," *Coord. Chem. Rev.* 1997, p. 166. As noted by Parker, the cyclization reactions when forming medium- and large-ring cyclic polyamines have an unfavorable entropy term to the overall free energy change. This makes it difficult to form cyclic polyaza compounds of medium and large ring sizes. To minimize this adverse thermodynamic effect and to inhibit the formation of undesired products, protective groups are typically added to the nitrogen groups of the linear starting materials. Another means of promoting the reaction is by template syntheses whereby the nitrogen groups that must be joined through a linkage to achieve the desired ring closure are placed in proximity to encourage them to react. A still further alternative is the use of reactive groups on the appropriate nitrogen atoms that are selective toward reaction with each other. In all of these reactions, polymerization competes with cyclization, and cyclization is typically the favored reaction only when the reactants are highly dilute.

The most common methods of forming the cyclic polyaza backbone are those that begin with a linear polyaza compound containing two primary amine groups and varying numbers of secondary amine groups, and proceed by adding one protective group to each of the nitrogen atoms of the linear compound, a typical protective group being p-toluene sulfonyl ("tosyl"). The two amine groups that still contain a H atom (i.e., the amine groups that were originally primary amine groups) are then reacted with a bridging reagent containing two reactive groups capable of undergoing nucleophilic reactions. Examples of bridging groups that are used for this purpose are ditosylated diols, such as for example ditosylated ethylene glycol. The bridging reaction is performed under conditions that do not allow for quaternization of the protected secondary amine groups. The bridging reaction produces a cyclic polyamine backbone of the desired size in which one protective group (such as a tosyl group) is attached to each nitrogen atom in the cycle. Various side products are produced as well. The protected cyclic polyamine is purified and subjected to reactions to remove the protective groups. (When the protective groups are tosyl groups, for example, deprotection is achieved by heating the tosylated cyclic polyamines in strong acid at elevated temperatures.) The deprotected cyclic polyamine product is then purified from the reaction mixture, and additional reactions are performed to attach the desired pendant arms to the nitrogen groups, the pendant arms being groups that are capable of coordinating metal cations.

Template methods have been used in the preparation of a limited number of cyclic polyamines. One such polyamine is cyclam, and a description of its synthesis using a template method is offered by Barefield, E. K., et al., *Inorg. Synth.,* vol. 16, p. 220 (1976). When metal cation (for example, nickel) is used as the template, the cation must be removed from the reaction mixture to obtain the free cyclic polyamine. The procedure for removing the metal cation often introduces contaminants that must themselves be removed before the cyclic polyamine can be reacted further in syntheses to generate the N-substituted cyclic polyamine chelator.

Cyclization can also be achieved by amide formation, since primary amines are typically favored over secondary amines in reactions between esters and amine groups to form amides. Thus, moderate yields of cyclic compounds containing two amide groups can be obtained in some cases by reacting a linear polyamine containing two primary amine groups with a bridging compound containing two ester groups. An example is the reaction between dipropylamine triamine with the diethyl ester of malonic acid, described by Helps, I. M., et al., *J. Chem. Soc. Perkin Trans. I* (1989), 2079. This reaction can be followed by reduction of the amide bonds to form the desired amines. As in methods described above, cyclization competes with polymerization, and to achieve selectivity toward cyclization the reactants in these amide formation reactions are typically used in dilute concentrations. Even with dilute reaction mixtures, the yields of the cyclic diamides are often modest, and reduction of the amide bonds and subsequent purification of the desired cyclic polyamine may prove difficult.

A further synthesis route is based on the tendency of α-chloroacetamides to favor reaction with secondary amines. In high dilution, therefore, one can produce certain cyclic diamides by reacting bis-α-chloroacetamides with certain secondary amines. A disclosure of this reaction is offered by Krakowiak, K. E., et al., *Synlett.* (1993), 611. The resulting diamide is then reduced to obtain the desired cyclic polyamine. This synthesis can only produce cyclic polyamines containing four or more nitrogen groups, and as in the above-described methods, requires highly dilute reactants to favor cyclization over polymerization.

Difficulties also exist in syntheses of N-monoalkylated amines that still contain H atoms attached to one or more of the N atoms, and in which the alkyl substitution on each N atom is a pendant arm capable of coordinating metal cations. Iveson, P. B., et al., "Monitoring the Moedritzer-Irani Synthesis of Aminoalkyl Phosphonates," Polyhedron, vol. 12, no. 19, pp. 2313–23 (1993) demonstrate that primary amines once substituted are disubstituted at a much greater rate than the initial substitution, thereby favoring disubstitution of the primary amine rather than monosubstitution. This difficulty is evidenced by the fact that there are no published reports of direct synthesis of either N,N',N"-tris (methylenephosphonic acid)-1,4,7-triazaheptane (in which each nitrogen is monosubstituted with a methylenephosphonate moiety) or its esterified products.

SUMMARY OF THE INVENTION

A novel process for the cyclization of polyamines has now been discovered that produces the cyclic product in high yield and at low cost, and is capable of doing so in concentrated solutions rather than dilute solutions. The polyamines that are addressed by this process are those in which all nitrogen atoms except two are fully substituted, the remaining two bearing only one H atom. Some or all of the nitrogen atoms are monosubstituted with pendant arms capable of coordinating metal cations, or with precursors that can be converted to such pendant arms by simple chemical reactions. The cyclization is performed by the use of a bridging agent containing two sites that each bear a reactive group capable of undergoing a nucleophilic attack by one of the N-H groups on the polyamines. When such nucleophilic attack is on an oxo group the intermediate formed is subsequently reduced to form the desired product. This invention also resides in a novel process for the introduction of no more than one methylenephosphonate ester groups as substituents on the nitrogen atoms of linear polyamines, by reacting the polyamines with a trisubstituted phosphite and a source of formaldehyde in the presence of water. The process results in the placement of one methylenephosphonate ester group on each primary and secondary nitrogen atom. The resulting methylenephosphonate ester-substituted linear polyamines can then be cyclized in accordance with the cyclization reaction described above, and hydrolysis of the some or all of the ester groups to acid groups can be performed either on the linear product or on the cyclic product. Still further, this invention resides in a novel class of N,N',N"-tris(methylene-phosphonate or methylenephosphonic acid-substituted)-1,4,7-triazaheptanes.

DETAILED DESCRIPTION OF THE INVENTION AND SPECIFIC EMBODIMENTS

In the aspects of this invention that relate to the cyclization of polyamines, the starting polyamine has the formula

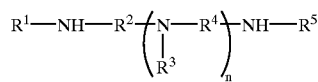

in which:
- $R^1$ and $R^5$ are either the same or different and are substituents capable of coordinating metal cations, or precursors that are convertible to such substituents,
- $R^2$ and $R^4$ either the same or different and are unsubstituted or substituted alkyl, aryl, alkylaryl, or alkylarylalkyl groups, $R^3$ is either:
  (a) a pendant arm capable of coordinating a metal cation, a precursor convertible to such a pendant arm, or an unsubstituted or substituted alkyl, aryl, alkylaryl, or alkylarylalkyl group, or
  (b) a divalent unsubstituted or substituted alkyl radical forming a cyclic group with either $R^2$ or $R^4$ and the N atom to which $R^3$ is bonded, and n is 0, 1, 2, 3, 4, 5, or 6.

When n is 2 or greater, the $R^3$s may be the same or different, although still within the above definition of $R^3$, and likewise the $R^4$s may be the same or different, although still within the above definition of $R^4$. For embodiments in which $R^3$ falls within part (b) of its definition, the starting compound already bears a cyclic structure but still contains the two N-H groups available for the cyclization reaction of this invention.

The cyclic compound produced by the cyclization reaction of this invention has the formula

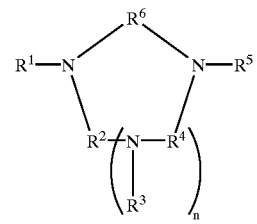

in which $R^6$ is an unsubstituted or substituted alkyl, aryl, alkylaryl, or alkylarylalkyl group.

Throughout this specification and claims, the term "alkyl" is used to denote any saturated hydrocarbyl group, branched, unbranched, or cyclic. Acyclic alkyl groups are preferred, and unbranched acyclic alkyl groups are particularly preferred. As the formulas indicate, alkyl groups in the definitions of $R^2$, $R^4$, and $R^6$ are divalent alkyl groups, while those in the definitions of $R^3$ are monovalent alkyl groups. In the definitions of $R^2$, $R^4$, and $R^6$, preferred alkyl groups are $C_1$–$C_6$ alkyl, and the most preferred are $C_2$–$C_4$ alkyl. The term "aryl" is used to denote the phenyl group and fused aromatic hydrocarbyl groups such as naphthyl, and phenanthryl. The preferred aryl group is phenyl. The term "substituted" is used to denote substituents that are inert to the reaction.

While $R^3$ is defined as either a pendant arm or a portion of an additional cyclic structure with the adjacent atoms, preferred $R^3$s are pendant arms, and preferred pendant arms are alkyl phosphonic acids, dialkyl esters of alkyl phosphonic acids, diaryl esters of alkyl phosphonic acids, and alkyl aryl esters of alkyl phosphonic acids. The "alkyl" in the term "alkyl phosphonic acid" denotes a divalent alkyl group the links the phosphorus atom to the nitrogen atom. Preferred divalent alkyl groups within this definition are $C_1$–$C_4$ alkyl, more preferred are $C_1$–$C_2$ alkyl, and the most preferred is the methylene group. On the ester portion of the group, the preferred groups are alkyl groups, particularly $C_1$–$C_6$ alkyl, and the most preferred are $C_1$–$C_3$ alkyl.

The bridging agent is a reactant having two reactive sites that will undergo a nucleophilic attack by the two N-H groups on the starting polyamine to place the $R^6$ bridge in the location shown in the formula of the cyclized product. Nucleophilic reactions are well known among those skilled in synthetic chemistry, and the groups that will serve effectively in the nucleophilic reactions at the two reactive sites on the bridging agent will be readily apparent to the skilled organic chemist. Examples of these groups are oxo, alkyl or aryl halides, and p-toluene sulfonate. The term "oxo" denotes an oxygen atom joined to a carbon atom on the bridging agent through a double bond, and bridging agents that contain oxo groups as the electrophiles are either aldehydes or ketones. Following nucleophilic attack on an oxo group the intermediate formed is reduced to form the desired product. The term "halide" denotes a halogen atom, of which fluoride, chloride, bromide, or iodide, with chloride and bromide are the most preferred. When the leaving groups are oxo groups, the reaction is preferably conducted in the presence of reducing agents, preferably hydrogen and an hydrogenation catalyst, examples of which are nickel, cobalt, copper, chromium, platinum, and palladium. A preferred hydrogenation catalyst is nickel. The residue of the bridging agent is defined by the definition given above for $R^6$.

The temperature at which the reaction is conducted can vary widely and is not critical to this invention. In general, the formation of undesired products and the degradation of the desired product can be minimized if the reaction temperature is maintained below 120° C. In the preferred practice of the cyclization reaction of the invention, the operating temperature is maintained within the range of about 20° C. to about 70° C. Likewise, the concentration of the reactants can vary and is not critical, although one advantage of the invention is that the reaction can be performed at concentrations higher than the processes of the prior art for forming the same products. Accordingly, in the preferred practice of this aspect of the invention, the concentration of the starting compound (i.e., the polyamine to be cyclized) is at least about 0.03 M, and most preferably from about 0.05 M to about 2.0 M.

The reaction can be performed either neat (i.e., in the absence of a solvent or in the presence of very little solvent) or in the presence of a solvent in significant amounts. When a solvent is used, protic solvents are preferred, and the most preferred among these are alcohols such as a $C_1$–$C_4$ alkyl alcohol.

In the aspects of this invention that relate to the incorporation of a methylenephosphonate ester into a linear polyamine, the starting material is a compound of the formula

in which $R^2$, $R^4$, and n are as defined above, a tri-substituted phosphite of the formula

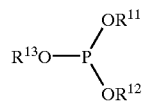

in which $R^{11}$, $R^{12}$, and $R^{13}$ are either the same or different and are each either alkyl or aryl, and a source of formaldehyde, the reaction being conducted in the presence of water. The terms "alkyl" and "aryl" are used here in the same manner as set forth above. The product of the reaction is a compound having the formula

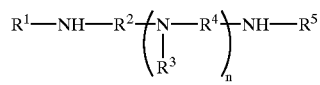

in which $R^1$, $R^3$, and $R^5$ are methylenephosphonate ester groups of the formula

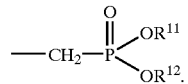

In preferred embodiments of this aspect of the invention, $R^2$ and $R^4$ are each $C_1$–$C_6$ alkyl and most preferably $C_2$–$C_4$ alkyl. Likewise, in preferred embodiments, $R^{11}$, $R^{12}$, and $R^{13}$ are each $C_1$–$C_6$ alkyl, and most preferably $C_1$–$C_3$ alkyl. Preferred values for n are 1 and 2.

The source of formaldehyde that is included among the reactants is any substance that will release formaldehyde for reaction with the polyamine and the tri-substituted phosphite in the reaction medium. Aqueous formaldehyde and paraformaldehyde are common sources of formaldehyde. Other sources of formaldehyde will be readily apparent to the skilled organic chemist. When aqueous formaldehyde is used the water associated with the formaldehyde may be a sufficient source of water in the reaction. When paraformaldehyde is used water must be introduced into the reaction from another source.

The conditions under which this reaction is conducted may vary and are not critical to this aspect of the invention. In the preferred practice of the invention, the reaction is conducted within operating conditions within certain ranges. The weight ratio of water to formaldehyde, for example, is preferably at least about 3:2. Likewise, the temperature at which the reaction is performed is preferably a maximum of about 40° C., and most preferably within the range of from about 10° C. to about 40° C. The reaction may also be conducted in the additional presence of a protic solvent other than water. Preferred such solvents are alcohols such as a $C_1$–$C_4$ alkyl alcohol.

Once the methylenephosphonate esters are bonded to the nitrogen atoms, the product can either be cyclized by action of the bridging agent in accordance with the reaction described above, and then may be subjected to hydrolysis reactions. Alternatively, the linear compound can be directly hydrolyzed to convert any number of the ester groups to acid form. Hydrolysis is performed by conventional techniques well known to the skilled organic chemist. Hydrolysis can be achieved by treatment with either acid or base. Hydrolysis in base typically results in hydrolysis of one of the ester groups on each phosphonate moiety, while hydrolysis in acid typically hydrolyzes both ester groups on each phosphonate moiety.

The hydrolysis reaction is illustrated on the non-cyclized polyamine as follows:

The starting material is a compound of the formula

in which $R^2$, $R^4$, and n are as defined above. This compound is reacted with a tri-substituted phosphite of the formula

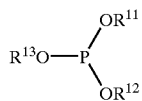

in which $R^{11}$, $R^{12}$, and $R^{13}$ are as defined above, and a source of formaldehyde in the presence of water. This reaction yields an intermediate of the formula

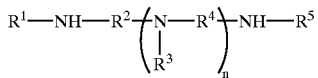

in which $R^1$, $R^3$, and $R^5$ are methylenephosphonate radicals of the formula

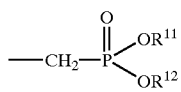

This intermediate is then hydrolyzed to convert $R^{11}$ to H. Preferably, any $R^{12}$ that is other than H is also converted to H.

New compositions of matter within the scope of this invention are the compounds having the formula

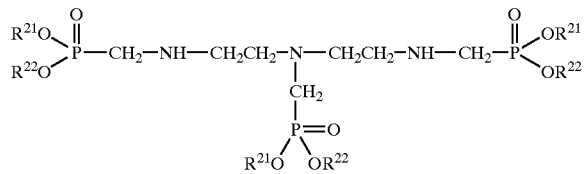

in which $R^{21}$ and $R^{22}$ are either the same or different, and are either H, alkyl, or aryl. The terms "alkyl" and "aryl" are as defined above. A preferred class of compounds are those in which $R^{21}$ and $R^{22}$ are either H or $C_1$–$C_6$ alkyl, and a further preferred class are those in which $R^{21}$ and $R^{22}$ are either H or $C_1$–$C_6$ alkyl. A still further preferred class are those in which these groups are either H or ethyl. Specific examples are N,N',N"-tris(methylene-phosphonate diethyl ester)-1,4,7-triazaheptane (the above formula in which $R^{21}$ and $R^{22}$ are each ethyl), N,N',N"-tris(methylenephosphonate ethyl ester)-1,4,7-triazaheptane (the above formula in which $R^{21}$ is H, and $R^{22}$ is ethyl), and N,N',N"-tris (methylenephosphonic acid)-1,4,7-triazaheptane (the above formula in which $R^{21}$ and $R^{22}$ are each H). These compounds and all others within the scope of the generic formula shown above are synthesized by the methods disclosed in this specification, and are useful for each of the uses set forth above in the "Description of the Prior Art" section of this specification.

The following examples are offered strictly for purposes of illustration.

EXAMPLE 1

This example illustrates the cyclization reaction of this invention, using the linear polyamine N,N',N"-tris (methylenephosphonate diethyl ester)-1,4,7-triazaheptane as the starting material.

The linear polyamine starting material (0.739 g) was added to 17 mL of methanol containing 0.11 g of nickel catalyst (ACTIMET C, obtained from Engelhardt De Meeren B. V., The Netherlands), and exposed to 10 atmospheres of $H_2$ gas at room temperature. To this mixture was added 0.99 g of 40% aqueous glyoxal in 10 mL of methanol at a slow rate over a 40-hour period. The final concentration of starting material in the reaction was 0.05 M. Two hours after the addition was completed, the reaction was analyzed by quantitative high-performance liquid chromatography (HPLC), and was found to contain 14.8% of the starting material and 78.7% of the product N,N',N"-tris(methylenephosphonate diethyl ester)-1,4,7-triazacyclononane (all by weight). Calibration of the HPLC for quantitative purposes was performed employing qualified standards. In similar experiments, the identity of the N,N',N"-tris (methylenephosphonate diethyl ester)-1,4,7-triazacyclononane was confirmed by chromatographic isolation followed by NMR analysis.

Similar results were obtained in a reaction in which the concentration of starting material in the reaction mixture was 0.24 M.

Those skilled in the art will recognize that these results indicate that similar success will be achieved with any linear polyamine as a starting material in which each nitrogen atom on the linear polyamine bears a single esterified pendant arm substituent, leaving single H atoms on only two nitrogen atoms. Hydrolysis of the ester groups on the esterified pendant arms yields acid groups that are capable of coordinating metal cations. This example illustrates that cyclization to form N-substituted cyclic polyamines in general is achieved by reductive alkylation employing a bridging reagent containing two aldehyde and/or ketone carbonyl groups and a suitable reducing agent.

EXAMPLE 2

(Comparative)

This example illustrates a prior art process for incorporating methylene phosphonate ester substituents onto the nitrogen atoms of 1,4,7-triazaheptane (diethylenetriamine). The process is disclosed by Hardy et al. in U.S. Pat. No. 4,394,330, and differs from the present invention by not including water in the reaction mixture.

According to the procedure described by Hardy et al., one equivalent of 1,4,7-triazaheptane was reacted neat with three equivalents of triethyl phosphite and three equivalents of paraformaldehyde at 70° C.±15° C. The Hardy et al. disclosure did not identify the products achieved at this stage but proceeded directly to add ethylene oxide. An elemental analysis was performed on the final product and the results were consistent with substituted 1,4,7-triazaheptane products containing three methylenephosphonate diethyl ester groups and two hydroxy ethyl groups. No data is provided by Hardy et al. that would indicate whether the final product (s) was a single well-defined species or a mixture of species.

The present inventors repeated the above procedure and analyzed by chromatography the product mixture resulting from the neat reaction at 70° C. between 1,4,7-triazaheptane, triethyl phosphite and paraformaldehyde. A chromatograph of the product mixture contained of at least five well-defined distinct peaks. This establishes that the synthesis procedure as described by Hardy et al. failed to produce high yields of the trialkylated N,N',N"-tris(methylenephosphonate diethyl ester)-1,4,7-triazaheptane.

EXAMPLE 3

(Comparative)

This example illustrates a further process outside the scope of this invention for incorporating methylene phosphonate ester substituents onto the nitrogen atoms of 1,4,7-triazaheptane (diethylenetriamine). This process differs from the present invention by not including water in the reaction mixture, and differs from the process used by Hardy et al. (Example 2 above) by being conducted at a lower temperature.

To a mixture of 1.03 g of 1,4,7-triazaheptane and 4.98 g of triethyl phosphite at room temperature were added 0.9 g of paraformaldehyde over a one-hour period with vigorous stirring. The reaction was allowed to proceed for 139 hours at room temperature. Chromatographic analysis revealed three main peaks. Quantitative HPLC analysis identified one of these peaks as the desired N,N',N"-tris (methylenephosphonate diethyl ester)-1,4,7-triazaheptane, but indicated that the yield of this compound was only 19%.

Similar reactions performed at temperatures in excess of 40° C. resulted in an even larger number of products and a lower yield of the desired product.

These results collectively demonstrate that performing the reaction under neat anhydrous conditions at temperatures below 40° C. resulted in fewer products than the same process at 40° C., but failed to produce high yields of the desired product.

EXAMPLE 4

(Comparative)

This example illustrates a further process outside the scope of this invention for incorporating methylene phosphonate ester substituents onto the nitrogen atoms of 1,4,7-triazaheptane (diethylenetriamine). This process differs from the present invention by not including water in the reaction mixture and by instead using 100% ethanol as a solvent.

To a solution of 1.0 g of 1,4,7-triazaheptane in 40 mL of absolute ethanol at room temperature was added 5.2 mL of triethyl phosphite. After the mixture was stirred for 15–30 minutes, 0.9 g of paraformaldehyde was added with vigorous stirring. The resulting mixture was stirred for five days at room temperature. Analysis of the product mixture by HPLC showed only traces of the desired trialkylated product, with the principal product being the dialkyalted N,N'-bis(methylenephosphonate diethyl ester)-1,4,7-triazaheptane.

This result demonstrates that when the reaction is performed at room temperature in the presence of paraformaldehyde and 100% ethanol but in the absence of water, the reaction does not produce a significant yield of the desired trialkylated product.

EXAMPLE 5

This example illustrates the process of this invention for incorporating methylene phosphonate ester substituents onto the nitrogen atoms of 1,4,7-triazaheptane (diethylenetriamine). The process in this example differs from those of Examples 2, 3, and 4 by including water in the reaction mixture.

To a mixture of 1.03 g of 1 ,4,7-triazaheptane and 4.98 g of triethyl phosphite were added 37% aqueous formaldehyde (2.24 g) at room temperature over a two-hour period with vigorous stirring. This resulted in a water:formaldehyde weight ratio of about 1.7:1. The reaction was allowed to proceed at room temperature for 71 hours. Quantitative HPLC analysis demonstrated a yield of 55% of the desired N,N',N"-tris(methylenephosphonate diethyl ester)-1,4,7-triazaheptane.

This result demonstrates that performing the neat reaction at room temperature employing an aqueous solution of formaldehyde containing a water:formaldehyde weight ratio exceeding 3:2 produces an improved yield of the desired product.

EXAMPLE 6

This example is a further illustration of the process of this invention for incorporating methylene phosphonate ester substituents onto the nitrogen atoms of 1,4,7-triazaheptane (diethylenetriamine). Ethanol is present in this example, and water is also present at varying ratios relative to formaldehyde.

To a mixture of 5.16 g of 1,4,7-triazaheptane in 50 mL of 96% ethanol were added 4.51 g of paraformaldehyde with vigorous mixing in an ice bath. The reaction mixture was allowed to reach room temperature, after which 26.02 g of triethyl phosphite were added over a two-hour period. After seven days of reaction, quantitative HPLC analysis established that the yield of the desired N,N',N"-tris (methylenephosphonate diethyl ester)-1,4,7-triazaheptane was 71%. Similar results were obtained in experiments at room temperature in which water or 50% to 96% ethanol was used as the solvent and either paraformaldehyde or aqueous formaldehyde was employed.

These results demonstrate that good yields of the desired product are obtained when water is present in the solvent.

EXAMPLE 7

This example illustrates the synthesis of N,N',N"-tris (dihydroxyphosphoryl-methyl diethyl ester)-1,4,7-triazaheptane.

To 5.25 g diethylenetriamine were added 24.9 g triethyl phosphite at room temperature. Formaldehyde (4.5 g) in the form of a 37% aqueous solution was added dropwise over a seven (7)-hour period with vigorous stirring. Stirring was continued overnight. Excess ethanol was removed under vacuum. Yield based on residue weight and chromatographic analysis of residue composition was approximately 64% of theoretical. Mass spectroscopic analysis following chromatographic purification demonstrated a peak of 553 daltons. In similar experiments the product was reacted with benzoyl chloride and the resultant product was separated and purified by chromatography. Proton NMR of this product was consistent with N, N" dibenzoyl-N,N',N"-tris [dihydroxyphosphorylmethyl diethyl ester]-1,4,7-triazaheptane. These results demonstrated the identity of the initial product of the reaction as N,N',N"-tris (dihydroxyphosphorylmethyl diethyl ester)-1,4,7-triazaheptane.

EXAMPLE 8

This example illustrates the synthesis of N,N',N"-tris (dihydroxyphosphoryl-methyl ethyl ester)-1,4,7-triazaheptane.

N,N',N"-tris(dihydroxyphosphorylmethyl diethyl ester)-1,4,7-triazaheptane was refluxed in 2N NaOH for 18 hours. The pH was adjusted to approximately 2 with HCl and the reaction mixture evaporated to dryness under educed pressure. Ethanol was added. Following trituration with ethanol the undissolved salts were removed by filtration. The ethanol was evaporated to dryness under reduced pressure. Isopropanol was added to the residue. Following trituration with isopropanol the undissolved salts were removed by filtration. The solvent was removed by filtration yielding the solid product as its Hcl salt. This product was characterized by proton NMR. The NMR was consistent with N,N',N'-tris (dihydroxyphosphorylmethyl ethyl ester)-1,4,7-triazaheptane.

EXAMPLE 9

This example illustrates the synthesis of N,N',N''-tris (dihydroxyphosphoryl-methyl)-1,4,7-triazaheptane.

N,N',N''-tris(dihydroxyphosphorylmethyl diethyl ester)-1,4,7-triazaheptane was heated at 100° C. in concentrated HCl for eight (8) hours. The acid was removed under vacuum distillation and the residue purified by chromatography. The purified product was characterized by proton NMR. The NMR was consistent with N,N',N''-tris (dihydroxy-phosphorylmethyl)-1,4,7-triazaheptane.

The foregoing is offered primarily for purposes of illustration. It will be readily apparent to those skilled in the art that further modifications and variations can be made that will still fall within the basic concepts of this invention.

What is claimed is:

1. A process for the manufacture of a cyclic compound having the formula

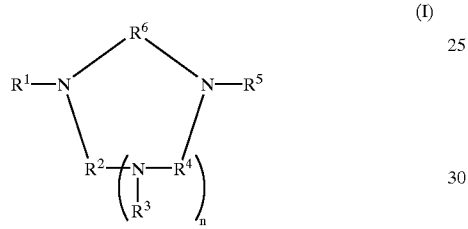

(I)

in which:

$R^1$, $R^3$, and $R^5$ are methylenephosphonate esters of the formula

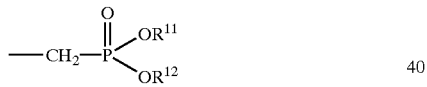

in which $R^{11}$ and $R^{12}$ are members independently selected from the group consisting of alkyl and aryl, $R^2$ and $R^4$ are members independently selected from the group consisting of unsubstituted and substituted divalent alkyl, divalent aryl, divalent alkylaryl, and divalent alkylarylalkyl groups, $R^6$ is a member selected from the group consisting of unsubstituted and substituted divalent alkyl, divalent aryl, divalent alkylaryl, and divalent alkylarylalkyl groups, and n is 0, 1, 2, 3, 4, 5 or 6, said process comprising:

(a) reacting a compound having the formula

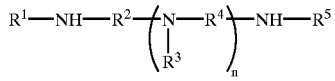

with a tri-substituted phosphite of the formula

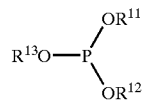

in which $R^{13}$ is a member selected from the group consisting of alkyl and aryl, p2 and a source of formaldehyde in the presence of water, to yield a substituted polyamine having the formula

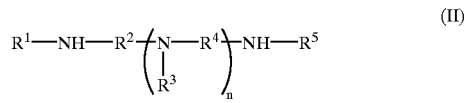

(II)

and (b) reacting said substituted polyamine with a bridging agent which contains leaving groups capable of participating in a nucleophilic reaction with the NH groups of said starting compound of Formula II to yield the $R^6$ bridge of said cyclic compound of Formula I.

* * * * *